United States Patent
Yang et al.

(10) Patent No.: US 9,877,697 B2
(45) Date of Patent: Jan. 30, 2018

(54) SYSTEMS, METHODS AND COMPUTER READABLE STORAGE MEDIA STORING INSTRUCTIONS FOR GENERATING PLANNING IMAGES BASED ON HDR APPLICATORS

(71) Applicant: EMORY UNIVERSITY, Atlanta, GA (US)

(72) Inventors: Xiaofeng Yang, Atlanta, GA (US); Tian Liu, Atlanta, GA (US); Peter J. Rossi, Atlanta, GA (US)

(73) Assignee: Emory University, Atlanta, GA (US)

( * ) Notice: Subject to any disclaimer, the term of this patent is extended or adjusted under 35 U.S.C. 154(b) by 0 days.

(21) Appl. No.: 14/700,463

(22) Filed: Apr. 30, 2015

(65) Prior Publication Data
US 2015/0313571 A1 Nov. 5, 2015

Related U.S. Application Data

(60) Provisional application No. 61/986,410, filed on Apr. 30, 2014.

(51) Int. Cl.
*G06K 9/00* (2006.01)
*A61B 8/08* (2006.01)
(Continued)

(52) U.S. Cl.
CPC .......... *A61B 8/0841* (2013.01); *A61B 8/5246* (2013.01); *A61B 8/5261* (2013.01);
(Continued)

(58) Field of Classification Search
None
See application file for complete search history.

(56) References Cited

U.S. PATENT DOCUMENTS 6,129,670 A * 10/2000 Burdette .................. A61B 8/12
600/427

6,208,883 B1 3/2001 Holupka et al.
(Continued)

FOREIGN PATENT DOCUMENTS

EP 1088524 A1 4/2001
WO 2013134782 A1 9/2013

OTHER PUBLICATIONS

Alexa et al. "Computing and Rendering Point Set Surfaces." IEEE Transactions on Visualization and Computer Graphics, 2003; 9(1): 3-15.
Baek et al. "Accuracy of volume measurement using 3D ultrasound and development of CT-3D US image fusion algorithm for prostate cancer radiotherapy." Medical Physics, 2013; 40(2): 021704-1-021704-13.

(Continued)

*Primary Examiner* — Nancy Bitar
(74) *Attorney, Agent, or Firm* — Emory Patent Group

(57) ABSTRACT

Systems, methods, and computer-readable storage media relate to generate an integrated image based on one or more applicators inserted into a target of a patient. The method may include receiving ultrasound image data and planning image data of the target. The ultrasound image data including a pre-operative and post-operative image data and the planning image data may include post-operative image data (e.g., CT and/or MRI image data). The method may include processing the ultrasound image data and the planning image data to determine a location of each channel and/or needle. The method may include generating an integrated image including the ultrasound image data and the planning image data based on the location of each channel and/or needle of the applicator. The methods, systems, and computer readable media according to embodiments can improve target (e.g., prostate) delineation, enable accurate dose planning and delivery, and potentially enhance HDR treatment outcome.

16 Claims, 7 Drawing Sheets

(51) Int. Cl.
  *A61N 5/10* (2006.01)
  *G06T 3/00* (2006.01)
  *G06T 7/33* (2017.01)
  *A61B 6/00* (2006.01)

(52) U.S. Cl.
  CPC ......... *A61N 5/1027* (2013.01); *A61N 5/1037* (2013.01); *G06T 3/0068* (2013.01); *G06T 7/33* (2017.01); *A61B 6/5247* (2013.01); *G06T 2207/10081* (2013.01); *G06T 2207/10132* (2013.01); *G06T 2207/30081* (2013.01)

(56) References Cited

U.S. PATENT DOCUMENTS

| | | | |
|---|---|---|---|
| 6,438,401 | B1 | 8/2002 | Cheng et al. |
| 6,512,942 | B1* | 1/2003 | Burdette ............... A61B 34/20 600/3 |
| 7,652,259 | B2 | 1/2010 | Kimchy ................. A61B 1/05 250/370.08 |
| 8,948,471 | B2* | 2/2015 | Fichtinger ............ A61B 6/504 382/128 |
| 2001/0041838 | A1* | 11/2001 | Holupka ............... A61B 34/20 600/439 |
| 2003/0065260 | A1* | 4/2003 | Cheng ................. A61B 8/0833 600/427 |
| 2004/0225174 | A1 | 11/2004 | Fuller et al. |
| 2006/0237652 | A1* | 10/2006 | Kimchy ................. A61B 1/05 250/363.02 |
| 2008/0262345 | A1 | 10/2008 | Fichtinger et al. |
| 2008/0287827 | A1* | 11/2008 | Sarkar ................... A61B 8/587 600/567 |
| 2009/0014015 | A1 | 1/2009 | Tutar et al. |
| 2010/0198063 | A1 | 8/2010 | Huber et al. |
| 2010/0240997 | A1* | 9/2010 | Ichioka ................... A61B 8/00 600/443 |
| 2010/0312038 | A1 | 12/2010 | Shechter |
| 2011/0166410 | A1 | 7/2011 | Gutierrez et al. |
| 2012/0157748 | A1 | 6/2012 | Sioshansi et al. |
| 2012/0271094 | A1 | 10/2012 | Fuller |
| 2013/0211230 | A1 | 8/2013 | Sperling |
| 2014/0303423 | A1* | 10/2014 | Amthor ................. A61N 5/1027 600/8 |
| 2015/0018666 | A1* | 1/2015 | Madabhushi ............ A61B 8/12 600/411 |

OTHER PUBLICATIONS

Even et al. "High-dose-rate prostate brachytherapy based on registered transrectal ultrasound and in-room cone-beam CT images." Brachytherapy, 2014; 13: 128-136.

Fallavollita et al. "Registration between ultrasound and fluoroscopy or Ct in prostate brachytherapy." Medical Physics, 2010; 37(6): 2749-2760.

Firle et al. "Registration of 3D U/S and CT images of the Prostate." CARS 2002 Computer Assisted Radiology and Surgery: Proceedings of the 16th International Congress and Exhibition. 2002; 1-6; Springer-Verlag Berlin Heidelberg, NY.

Firle et al. "Validation of 3D Ultrasound-CT Registration of Prostate images." Proceedings of SPIE International Conference on Medical Imaging, 2003; 354-362.

Fuller et al. "Computed tomography-ultrasound fusion brachytherapy: Description and evolution of the technique." Brachytherapy, 2007; 6: 272-279.

Gong et al. "Ultrasonography and Fluoroscopic Fusion for Prostate Brachytherapy Dosimetry." International Journal of Radiology Oncology Biology Physics, 2002; 54(5): 1322-1330.

Ng et al. "A dual modality phantom for cone beam CT and ultrasound image fusion in prostate implant" Medical Physics, 2008; 35(5): 2062-2071.

Nuver et al. "HDR Prostate Brachytherapy Based on Registered TRUS and In-Room Cone-Beam CT Images." ASTRO 55th Annual Meeting, 2013; Poster No. 2449.

Polo, Alfredo. "Image fusion techniques in permanent seed implantation." Journal of Contemporary Brachytherapy, 2010; 2(3): 98-106.

Qiu et al. "Needle segmentation using 3D Hough transform in 3D TRUS guided prostate transperineal therapy." Medical Physics, 2013; 40(4): 042902-1-042902-13.

Steggerda et al. "The applicability of simultaneous TRUS-CT imaging for the evaluation of prostate seed implants." Medical Physics, 2005; 32(7): 2262-2270.

Torsello et al. "Sampling Relevant Points for Surface Registration," 2011 International Conference on 3D Imaging, Modeling, Processing, Visualization and Transmission, 2011; 290-295.

Yang et al. "3D Non-rigid Registration Using Surface and Local Salient Features for Transrectal Ultrasound Image-guided Prostate Biopsy." Proceedings of SPIE, 2011; 1-10.

\* cited by examiner

SYSTEMS, METHODS AND COMPUTER READABLE STORAGE MEDIA STORING INSTRUCTIONS FOR GENERATING PLANNING IMAGES BASED ON HDR APPLICATORS

CROSS REFERENCE TO RELATED APPLICATION

This application claims priority to Provisional Application Ser. No. 61/986,410 filed Apr. 30, 2014, which is hereby incorporated by reference in its entirety.

BACKGROUND

Radiotherapy is an important treatment modality for prostate cancer. The technological advances in real-time ultrasound image guidance for High-Dose-Rate (HDR) prostate brachytherapy have placed this treatment modality at the forefront of innovation in the field of cancer radiotherapy. HDR prostate brachytherapy generally involves using a radiation source (Iridium-192) to deliver high radiation dose to the prostate gland through a series of applicators that are temporarily placed within the prostate transperineally under the transrectal ultrasound guidance. The dose decreases exponentially with increasing distance from the radioactive source according to the inverse-square law. This procedure allows the dose delivered to the surrounding normal tissues to be minimized.

Recent data shows an improved efficacy of this treatment approach in patients with locally advanced cancer when compared with conventional external beam radiotherapy. As a result, an increasing number of men, many of younger ages, have been undergoing prostate HDR brachytherapy instead of radical prostatectomy for localized prostate cancer.

One key to the success of the HDR prostate brachytherapy is the accurate localization of the prostate, for example, in the treatment-planning images. If the prostate is not accurately localized, a high therapeutic radiation dose could be delivered to the surrounding normal tissues (e.g. rectum and bladder) during the treatment. This may cause severe complications such as rectum bleeding and lead to an undertreatment of the cancerous regions within the prostate gland; therefore result in poor treatment outcome.

Treatment-planning images are often computer tomography (CT) images. However, CT images can have poor soft-tissue contrast and thus lead to inaccurate prostate localization and inaccurate treatment planning. The accuracy and reproducibility of prostate volume manually contoured on CT images among physicians has been found to be poor. It has been shown that CT-based prostate contours consistently overestimate the prostate volume by 30% to 50%.

SUMMARY

Thus, there is a need for accurate prostate localization, for example, by improving the accuracy of the prostate contour. This can enable accurate treatment planning and delivery, and therefore can improve the outcomes from HDR treatments.

This disclosure generally relates to methods, systems, and computer readable storage media that include instructions to integrate intra-operative ultrasound-based target volume into treatment planning through fusion based on the applicator locations.

In some embodiments, the methods may relate to a computer-implemented method to generate an integrated image based on or more applicators inserted into a target of a patient, each applicator including at least one channel and/or needle. In some embodiments, the method may include receiving ultrasound image data and planning image data of the target of the patient. The ultrasound image data may include a first set of ultrasound image data of the target before insertion of the one or more applicators and a second set of ultrasound image data of the target after the insertion of the one or more applicators. The planning image data may include image data of the target after the insertion of the planning image data being acquired from an imaging system different from ultrasound. In some embodiments, the method may include processing the ultrasound image data to determine a location of each channel and/or needle. The processing may include registering the first set of ultrasound image data and the second set of ultrasound image data. The method may further include processing the planning image data to determine a location of each channel and/or needle. The method may also include generating an integrated image including the ultrasound image data and the planning image data based on the location of each channel and/or needle.

In some embodiments, the computer-readable media may relate to a non-transitory computer readable storage medium comprising program instruction stored thereon, wherein the program instructions are executable by a computer to cause the computer to generating an integrated image based on one or more applicators inserted into a target of a patient by performing steps. Each applicator may include at least one channel and/or needle. In some embodiments, the steps may include receiving ultrasound image data and planning image data of the target of the patient. The ultrasound image data may include a first set of ultrasound image data of the target before insertion of the one or more applicators and a second set of ultrasound image data of the target after the insertion of the one or more applicators. The planning image data may include image data of the target after the insertion of the planning image data being acquired from an imaging system different from ultrasound. In some embodiments, the steps may include processing the ultrasound image data to determine a location of each channel and/or needle. The processing may include registering the first set of ultrasound image data and the second set of ultrasound image data. The steps may further include processing the planning image data to determine a location of each channel and/or needle. The steps may also include generating an integrated image including the ultrasound image data and the planning image data based on the location of each channel and/or needle.

In some embodiments, the systems may relate to a system for generating an integrated image based on or more applicators inserted into a target of a patient, each applicator including at least one channel and/or needle. The system may include at least one processor; and a memory. The processor may be configured to cause receiving ultrasound image data and planning image data of the target of the patient. The ultrasound image data may include a first set of ultrasound image data of the target before insertion of the one or more applicators and a second set of ultrasound image data of the target after the insertion of the one or more applicators. The planning image data may include image data of the target after the insertion of the planning image data being acquired from an imaging system different from ultrasound. In some embodiments, the processor may be configured to cause processing the ultrasound image data to determine a location of each channel and/or needle. The processing may include registering the first set of ultrasound image data and the second set of ultrasound image data. The processor may further be configured to cause processing the planning image data to determine a location of each channel and/or needle. The processor may also be configured to cause generating an integrated image including the ultrasound image data and the planning image data based on the location of each channel and/or needle.

Additional advantages of the disclosure will be series forth in part in the description which follows, and in part will be obvious from the description, or may be learned by practice of the disclosure. The advantages of the disclosure will be realized and attained by means of the elements and combinations particularly pointed out in the appended claims. It is to be understood that both the foregoing general description and the following detailed description are exemplary and explanatory only and are not restrictive of the disclosure, as claimed.

BRIEF DESCRIPTION OF THE DRAWINGS

The disclosure can be better understood with the reference to the following drawings and description. The components in the figures are not necessarily to scale, emphasis being placed upon illustrating the principles of the disclosure.

DETAILED DESCRIPTION OF THE EMBODIMENTS

Figure 1:
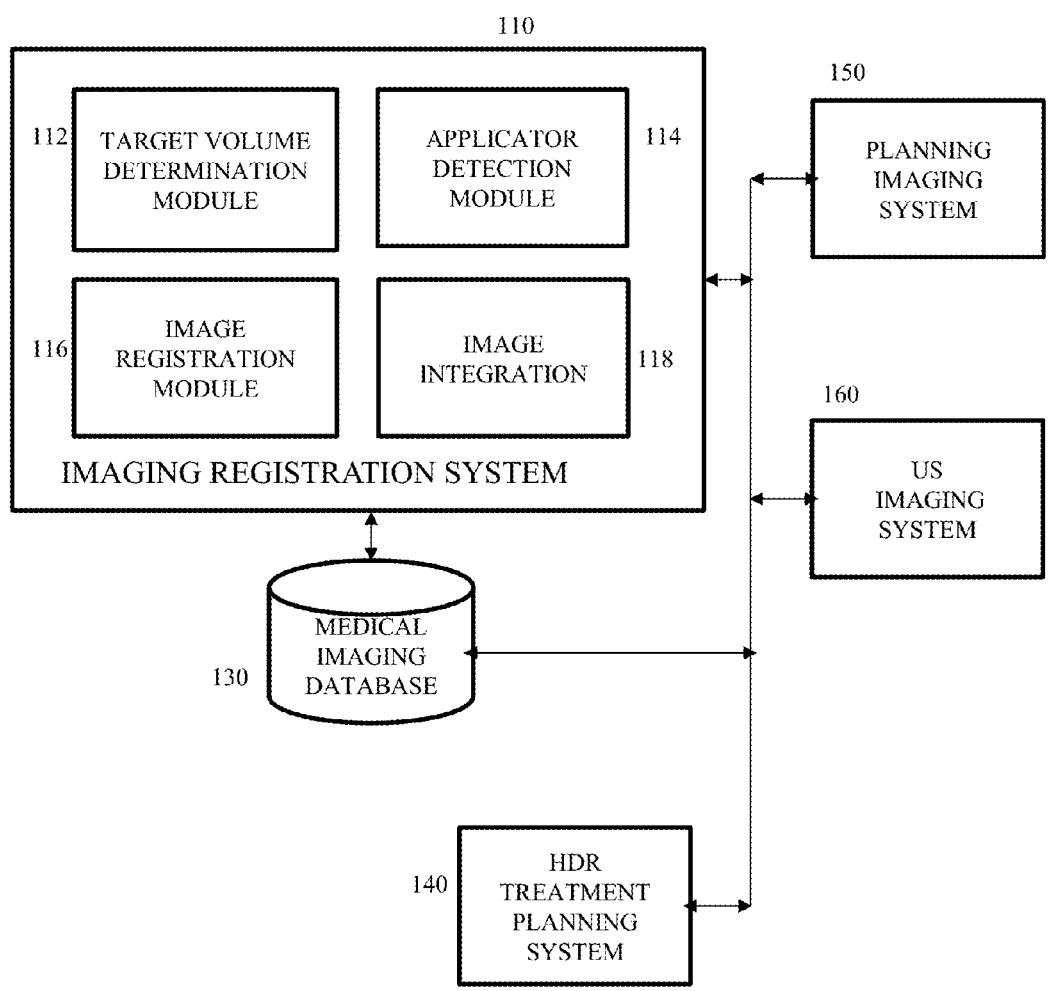
FIG. 1 shows a block diagram illustrating a system according to embodiments.

In the following description, numerous specific details are series forth such as examples of specific components, devices, methods, etc., in order to provide an understanding of embodiments of the disclosure. It will be apparent, however, to one skilled in the art that these specific details need not be employed to practice embodiments of the disclosure. In other instances, well-known materials or methods have not been described in detail in order to avoid unnecessarily obscuring embodiments of the disclosure. While the disclosure is susceptible to various modifications and alternative forms, specific embodiments thereof are shown by way of example in the drawings and will herein be described in detail. It should be understood, however, that there is no intent to limit the disclosure to the particular forms disclosed, but on the contrary, the disclosure is to cover all modifications, equivalents, and alternatives falling within the spirit and scope of the disclosure.

This disclosure generally relates to methods, systems, and computer readable storage media that generate an integrated image including the ultrasound image data and the planning image data based on the location of each channel and/or needle of an HDR applicator. The methods, systems, and computer readable media according to embodiments address the deficiencies of relying on planning images alone.

The methods, systems, and computer readable media according to embodiments can result in improved prostate contours; result in more efficient and faster procedure; and result in an improved registered image. The methods, systems, and computer readable media according to embodiments can improve prostate delineation, enable accurate dose planning and delivery, and potentially enhance prostate HDR treatment outcome.

The embodiments of the disclosure are described with respect to high dose rate (HDR) brachytherapy of a prostate of a human patient. It should be understood by one of ordinary skill in the art that the embodiments of the disclosure can be applied to other types of brachytherapy and other targets (such as other portions of the body), whether human or animal. The use of the method and system of the embodiments of the disclosure can also be adapted for other types of applicators.

FIG. 1 shows an example of a system 100 for generating planning images based on pre-operative ultrasound image data and post-operative planning image data based on one or more HDR brachytherapy applicators. An applicator may be any applicator having a plurality of channels and/or needles; a device including multiple channels and/or needles; a device having a plurality of applicators and/or needles; or an organ specific design; among others; or a combination thereof.

In some embodiments, the modules and/or systems of the system 100 may be connected to a data network, a wireless network, or any combination thereof. In some embodiments, any of the modules and/or systems of the system 100 may be at least in part be based on cloud computing architecture. In some embodiments, the modules and/or systems may be applied to a self-hosted private cloud based architecture, a dedicated public cloud, a partner-hosted private cloud, as well as any cloud based computing architecture. Although the modules of the system are shown as being directly connected, the modules may be indirectly connected to one or more of the other modules of the system. In some embodiments, a module may be only directly connected to one or more of the other modules of the system.

As shown in FIG. 1, the system 100 may include an ultrasound imaging system 160. In some embodiments, the ultrasound (US) imaging system 160 may be configured to acquire ultrasound images before and/or after the insertion of the applicator(s). In some embodiments, the system 160 may include two ultrasound systems. In some embodiments, for example, the ultrasound system 160 may include a TRUS ultrasound image system.

In some embodiments, the system 100 may include a planning imaging system 150. In some embodiments, the planning imaging system 150 may be configured to acquire post-operative planning images (after insertion of the applicator(s)). In some embodiments, the planning image system 150 may be a CT imaging system. In some embodiments, the planning system 150 may be other modality, for example, may be a MRI imaging system.

In some embodiments, the system 100 may include an imaging registration system 110 according to embodiments. The system 110 may be configured to acquire the image data from the imaging systems (e.g., 150 and/or 160) and/or a medical imaging database 130 configured to store medical imaging data.

The imaging registration system 110 according to embodiments may be configured to generate integrated post-operative images from more than one imaging modality based on the needles and/or channels of the applicator(s). In some embodiments, the system 110 may include a target volume determination module 112 configured to determine volume (or contours) of the target (e.g., prostate) from the ultrasound image data (pre-operative). In some embodiments, the system 110 may include an applicator detection module 114 configured to determine the locations of the needles and/or channels of the applicator(s) in the image data from the US imaging system 160 and the planning image system 150.

In some embodiments, the system 100 may include an image registration module 116 configured to register the image data from the planning image system 150 and the US imaging system 160 based on the determined locations of the needles and/or channels of the applicator(s). In some embodiments, the image integration module 118 may be configured to integrate the target volume into the registered image data.

In some embodiments, the system may include an HDR treatment planning system 140. The HDR treatment planning system may be configured to deliver HDR brachytherapy treatment based on the integrated images generated by the imaging registration system 110.

Figure 2:
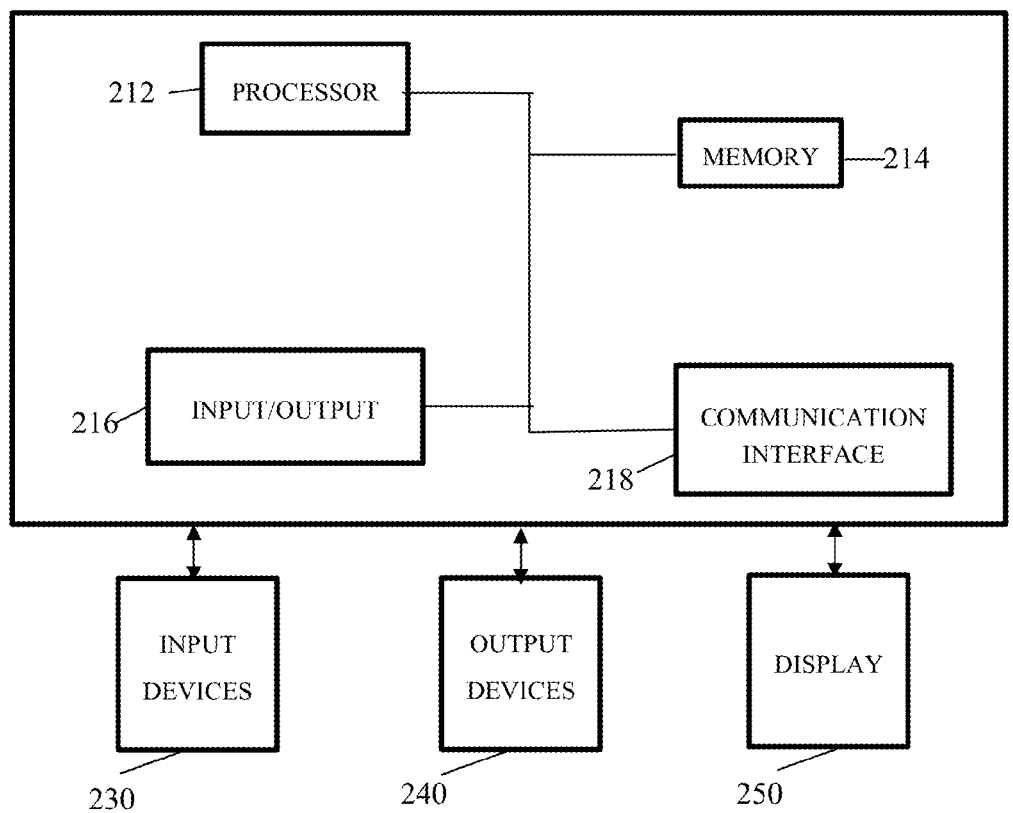
FIG. 2 shows a block diagram illustrating an example of a computing system.

One or more of the modules and/or systems of system 100 may be and/or include a computer system and/or device. FIG. 2 is a block diagram showing a computer system 200. The modules of the computer system 200 may be included in at least some of the systems and/or modules, as well as other devices of system 100.

The systems may include any number of modules that communicate with other through electrical or data connections (not shown). In some embodiments, the modules may be connected via a wired network, wireless network, or combination thereof. In some embodiments, the networks may be encrypted. In some embodiments, the wired network may be, but is not limited to, a local area network, such as Ethernet, or wide area network. In some embodiments, the wireless network may be, but is not limited to, any one of a wireless wide area network, a wireless local area network, a Bluetooth network, a radiofrequency network, or another similarly functioning wireless network.

It is also to be understood that the systems may omit any of the modules illustrated and/or may include additional modules not shown. It is also be understood that more than one module may be part of the system although one of each module is illustrated in the system. It is further to be understood that each of the plurality of modules may be different or may be the same. It is also to be understood that the modules may omit any of the components illustrated and/or may include additional component(s) not shown.

In some embodiments, the modules provided within the systems may be time synchronized. In further embodiments, the systems may be time synchronized with other systems, such as those systems that may be on the medical facility network.

The system 200 may be a computing system, such as a workstation, computer, or the like. The system 200 may include one or more processors 212. The processor(s) 212 (also referred to as central processing units, or CPUs) may be any known central processing unit, a processor, or a microprocessor. The processor(s) 212 may be coupled directly or indirectly to one or more computer-readable storage media (e.g., memory) 214. The memory 214 may include random access memory (RAM), read only memory (ROM), disk drive, tape drive, etc., or a combinations thereof. The memory 214 may be configured to store programs and data, including data structures. In some embodiments, the memory 214 may also include a frame buffer for storing data arrays.

The processor(s) 212 may be configured to determine location(s) of each needle and/or channel and generate an integrated image. In some embodiments, the processor(s) 212 may be capable of performing the image data processing. In other embodiments, the system may include a separate processor(s) (e.g., CPU) for performing the image data processing and/or generation of integrated image.

In some embodiments, another computer system may assume the data analysis or other functions of the processor(s) 212. In response to commands received from the input device, the programs or data stored in the memory 214 may be archived in long term storage or may be further processed by the processor and presented on a display.

In some embodiments, the system 210 may include a communication interface 218 configured to conduct receiving and transmitting of data between other modules on the system and/or network. The communication interface 218 may be a wired and/or wireless interface, a switched circuit wireless interface, a network of data processing devices, such as LAN, WAN, the internet, or combination thereof. The communication interface may be configured to execute various communication protocols, such as Bluetooth, wireless, and Ethernet, in order to establish and maintain communication with at least another module on the network.

In some embodiments, the system 210 may include an input/output interface 216 configured for receiving information from one or more input devices 230 (e.g., a keyboard, a mouse, and the like) and/or conveying information to one or more output devices 240 (e.g., a printer, a CD writer, a DVD writer, portable flash memory, etc.). In some embodiments, the one or more input devices 230 may configured to control, for example, the determination of the needle and/or channel locations and/or integrated image, display of the reconstructed needle(s) and/or channel(s) and/or integrated image on a display 250, printing of the images by a printer interface, among other things.

Figure 3:
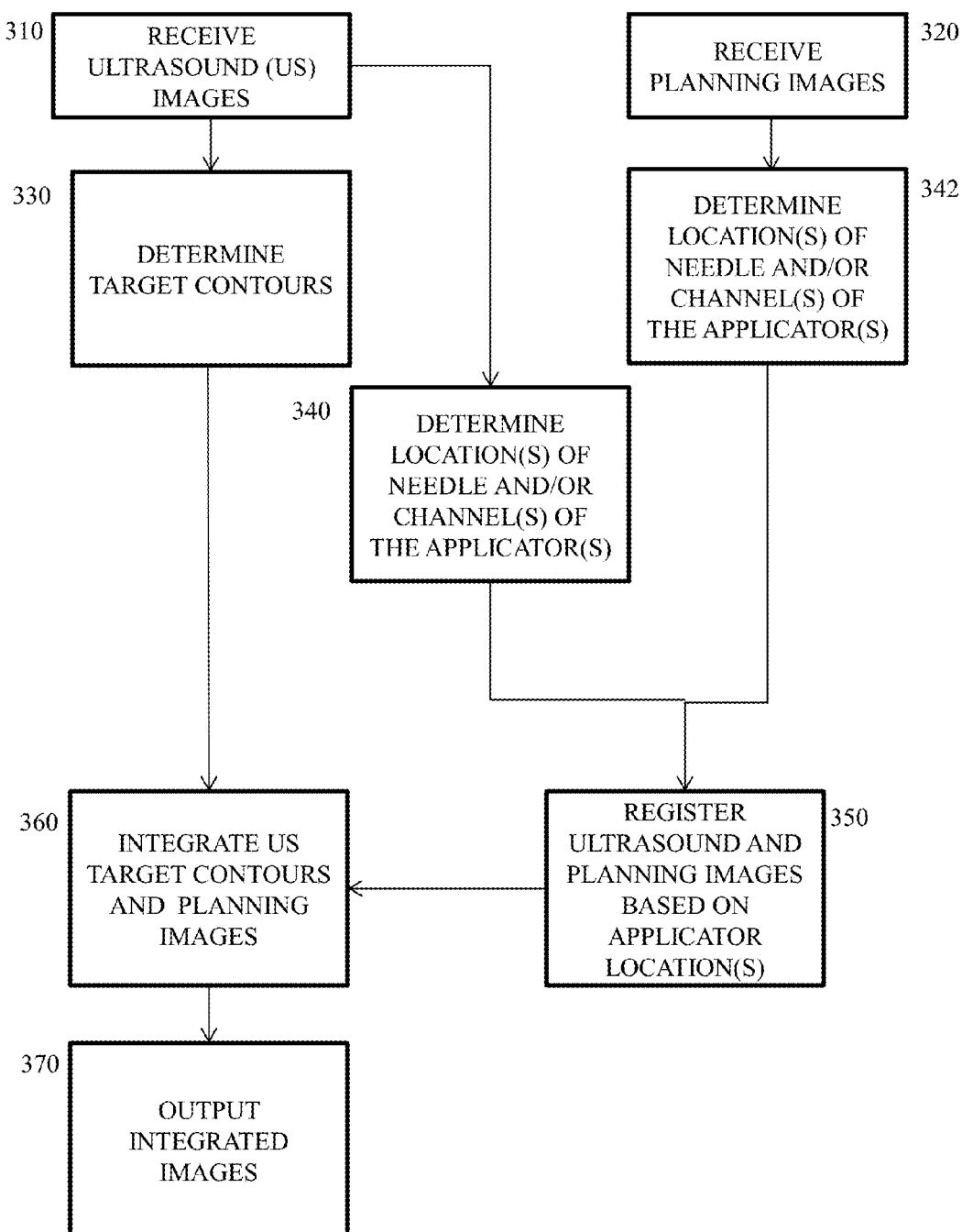
FIG. 3 shows a method of processing ultrasound image data and planning image data to generate an integrated image according to embodiments.

FIG. 3 illustrates a method 300 for generating integrated planning images based on one or more brachytherapy applicators according to embodiments. The system for carrying out the embodiments of the methods disclosed herein is not limited to the systems shown in FIGS. 1 and 2. Other systems may be used.

The methods of the disclosure are not limited to the steps described herein. The steps may be individually modified or omitted, as well as additional steps may be added. It will be also understood that at least some of the steps may be performed in parallel.

Unless stated otherwise as apparent from the following discussion, it will be appreciated that terms such as "identifying," "receiving," "integrating," "filtering," "combining," "reconstructing," "segmenting," "generating," "registering," "determining," "obtaining," "processing," "computing," "selecting," "estimating," "detecting," "tracking," "calculating," "comparing," "modifying," "aligning" "fusing," or the like may refer to the actions and processes of a computer system, or similar electronic computing device, that manipulates and transforms data represented as physical (e.g., electronic) quantities within the computer system's registers and memories into other data similarly represented as physical quantities within the computer system memories or registers or other such information storage, transmission or display devices. Embodiments of the methods described herein may be implemented using computer software. If written in a programming language conforming to a recognized standard, sequences of instructions designed to implement the methods may be compiled for execution on a variety of hardware platforms and for interface to a variety of operating systems. In addition, embodiments are not described with reference to any particular programming language. It will be appreciated that a variety of programming languages may be used to implement embodiments of the disclosure.

In some embodiments, the method 300 may include a step 310 of receiving (also referred to as "first") ultrasound image data. The ultrasound image data may include pre-operative (pre-applicator insertion) image data and post-operative (post-applicator insertion) image data. In some embodiments, the pre-operative image data may be acquired before the insertion of the brachytherapy applicator(s) into a target using an ultrasound system. The post-operative image data may be acquired after the insertion of the brachytherapy applicator(s) into the target but before the application of the high dose rate source into the applicator(s). In some embodiments, the image data may be received from the image acquisition device (e.g., 3D TRUS system) (e.g., US imaging system 160) and/or from a data storage device (e.g., the medical imaging database 130).

In some embodiments, the method 300 may include a step 320 of receiving (also referred to as "second image data") planning image data. The planning image data may be received from a data storage device (e.g., the medical imaging database 130) or the image acquisition device (e.g., the planning imaging system 150). The planning image data may be from a different imaging modality (than the data received in step 310). In some embodiments, the planning image data may be acquired by a CT system after the applicator insertion. In some embodiments, the planning image data may correspond to imaging modality data different from ultrasound acquired after the applicator insertion. In some embodiments, the planning image data may correspond to MRI image data acquired after the applicator insertion.

The image data received in steps 310 and/or 320 may be in a Digital Imaging and Communications in Medicine (DICOM) format. The image data may include header and image data. The header may include image information. The image information may include information regarding the scan. The image information may include but is not limited to pixel counts, acquisition angles, distance between the patient and the detector, distance between the source and the detector, number of frames, dimensions of the image, data resolution, and image size. The image data may be raw data or processed image data.

In some embodiments, the method 300 may include a step 330 of determining the target contours (e.g., prostate) using the ultrasound image data. The step 330 may be performed using any methods to contour the target (e.g., prostate) volume.

In some embodiments, the method 300 may include a step 340 of determining location(s) (with respect to the image (e.g., pixel location(s)) of the needles and/or channels of the applicator(s) in the ultrasound image data by reconstructing the needles and/or channels from the ultrasound image data and a step 342 of reconstructing the needles and/or channels from the planning image data. The steps 340 and 342 may be performed in parallel, sequentially, or a combination thereof. In some embodiments, a different method may be used.

In some embodiments, the location(s) of the needles and/or channels in the ultrasound image data may be determined by reconstructing the whole (e.g., body portion and tip portion) needle(s) and/or channel(s) and by reconstructing the tip portion of each needle and/or channel. The tip portion of each needle and/or channel corresponds to the starting position (also referred to as "tip position") of each needle and/or channel. The tip portion of the needles and/or channels refers to region of the needles and/or channels located closest to the base of the target (e.g., prostate)(and farthest away from the clinician) and the body portion of the needles and/or channels refers to region of the needles and/or channels that is visible in the image and that extends between the tip/starting position and base of the applicator (e.g., fixation element) that is farthest away from the base of the target (and closest to the clinician). By separately determining the tip position, the different geometries of applicators can be addressed thereby improving reconstruction of the applicator. By way of example, many applicators have bodies (body of the whole needle and/or channel) are cylindrical and tips that are cylindrical. The cylindrical tips can be affected by artifacts in ultrasound images and therefore can be difficult to determine using conventional methods.

Figure 4:
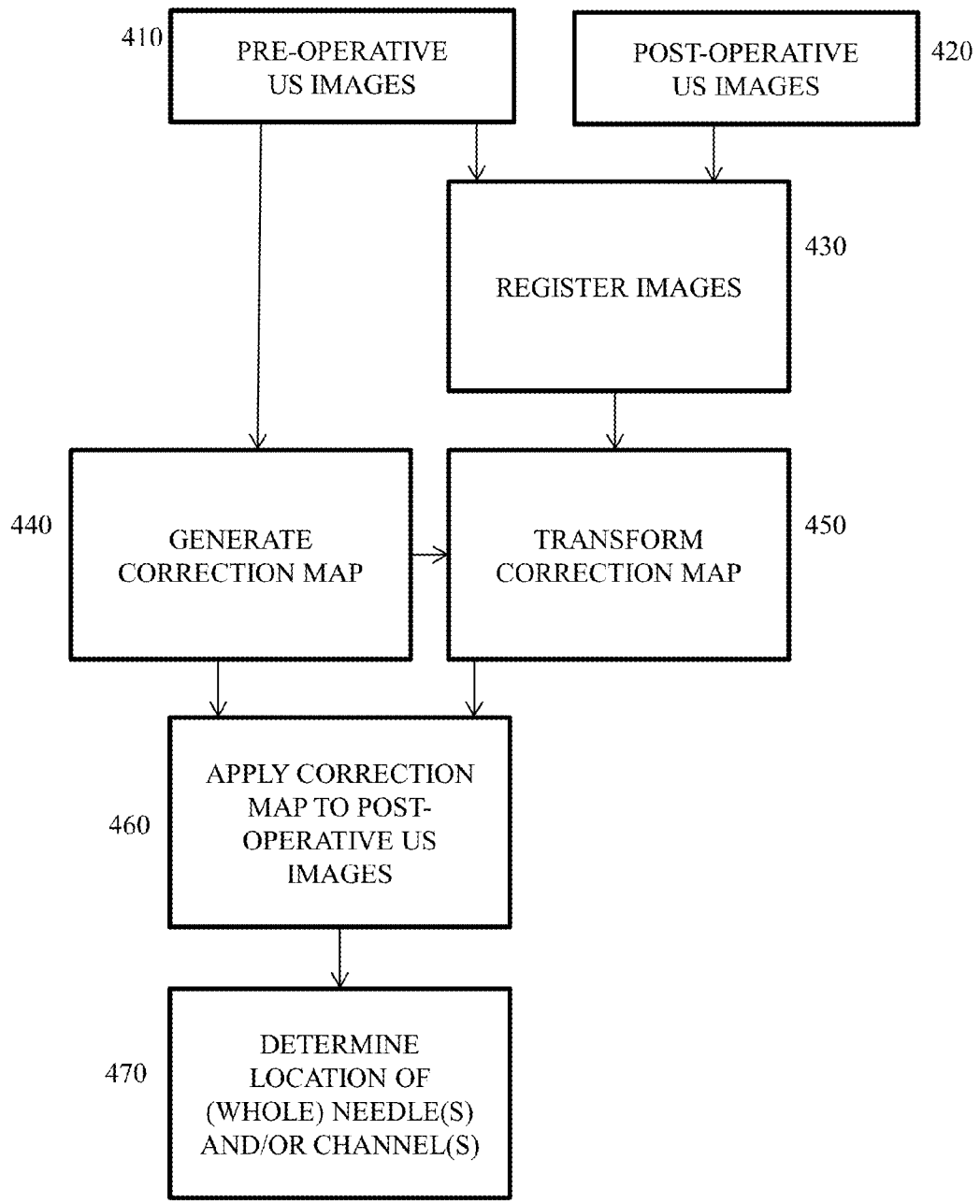
FIG. 4 shows a method of determining locations of the body portions and tip portions of the one or more applicators according to some embodiments.

FIG. 4 show an example of a method for determining the location(s) of the whole channel and/or needle of applicator from the ultrasound image data. FIG. 5 shows an example of the method of determining the starting position (e.g., tip) of each needle and/or channel from the ultrasound image data. In some embodiments, the starting position of each needle and/or channel may be first determined, for example, as shown in FIG. 5. The starting positions determined in FIG. 5 may be used as starting points to reconstruct the respective needle and/or channel according to the method of FIG. 4. In other embodiments, each needle and/or channel location may be reconstructing according to FIG. 4 and the starting positions of each needle and/or channel may be modified based on the starting positions determined in FIG. 5. In some embodiments, the reconstruction of the applicator(s) may be performed by other methods.

FIG. 4 shows a method 400 of determining the locations of the whole needles and/or channels by reconstructing the body portion and tip portion of the applicator(s) based on the ultrasound image data according to embodiments. In some embodiments, the method 400 may include a step 430 of registering pre-operative ultrasound data 410 and post-operative ultrasound data 420 using an intensity and feature-based registration method. For example, the registration may be achieved using a combination of an intensity-based similarity metric (such as, e.g., normalized mutual information) and a feature-based similarity metric (such as, e.g., normalized sum-of-squared differences metric).

Next, the method 400 may include a step 440 processing the ultrasound pre-operative data 410 to generate an attenuation correction map (e.g., a 3D correction map). The attenuation correction map may be generated by any method. In some embodiments, the attenuation correction map may be generated by applying an inhomogeneous correction filter to the pre-operative ultrasound image to generate a patient-specific attenuation correction map. In some embodiments, other methods may be used to generate attenuation correction map. For example, the attenuation correction map may be generated by universally applying a predetermined attenuation coefficient (e.g., 0.5 dB/MHZ/cm) to the pre-operative ultrasound image. This attenuation correction map can correct for intensity changes induced by various machine settings (e.g., time-gain-control) and tissue attenuation (ultrasound signal decreases while traveling though the tissue).

The method 400 may include a step 450 of transforming the correction map to the post-operative ultrasound data 420. Next, the method 400 may include a step 460 of applying the transformed correction map to the post-operative image data 420. The step 460 may include multiplying the transformed 3D correction map to the post-operative image data 420 to generate a corrected post-operative ultrasound images.

In some embodiments, the method 400 may include a step of detecting the needles and/or channels of the applicator(s) in the corrected post-operative ultrasound images by filtering and thresholding the intensity values, for example, using a predetermined range of one or more threshold values. The threshold(s) for the intensity values may depend on one or more factors, including but not limited to scan parameters, applicator materials, patient soft-tissue variations, among others, or a combination thereof. For example, for an 8-bit ultrasound image (intensity level 0-255), the threshold value may be 220.

Figure 5A:
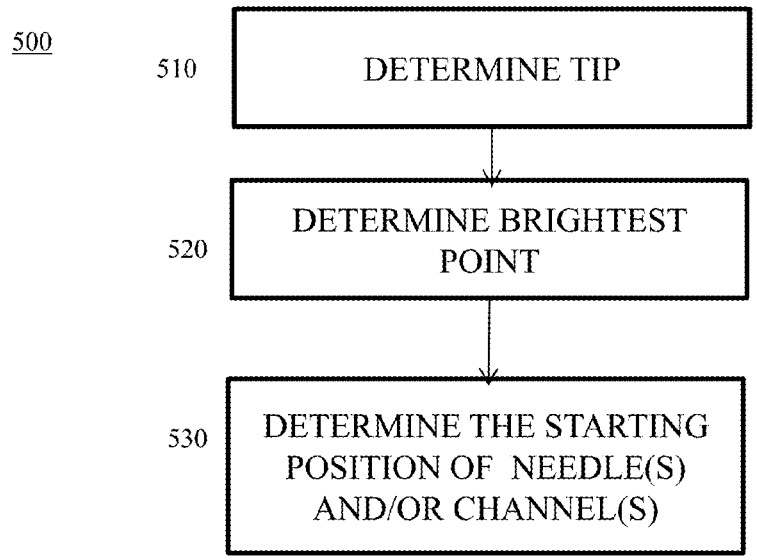
FIG. 5A shows a method of determining locations of the tip portions of each needle and/or channel of the applicator(s) according to other embodiments.

FIG. 5A shows a method 500 of determining the starting position (e.g., location of the tip portion) of each needle and/or channel of the applicator(s) in the ultrasound image data 310 by reconstructing based solely on the post-operative and attenuation-corrected ultrasound image data according to some embodiments. The method 500 may include a step 510 of determining the starting position (e.g., tip) of each needle and/or channel located close to the base of the target (e.g., prostate). In some embodiments, the starting position may be determined by determining the end point of the brightest point. Next, the method 500 may include a step 520 of determining an area of the highest intensity (e.g., the brightest point) of each needle and/or channel and identifying that region, for example, by placing a circle with the applicator diameter on the image (e.g., an axial TRUS image). In some embodiments, steps 510 and 520 may repeated for each image. In other embodiments, steps 510 and 520 may be applied to a portion of the images and the location of the starting position (tip) of each needle and/or channel in the remaining images may be determined by interpolation. In some embodiments, the method 500 may include a step 530 of reconstructing the starting positions of the needles and/or channels of the applicator(s) for the ultrasound images based on the identified regions. In some embodiments, the reconstruction may be 3D.

Figure 5B:
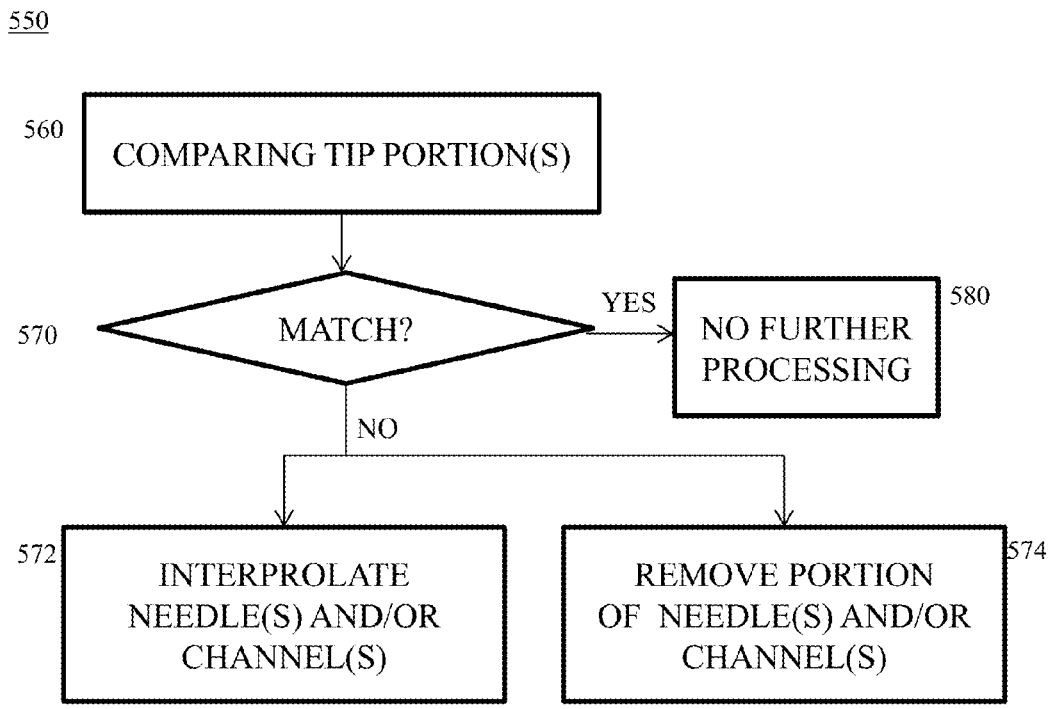
FIG. 5B shows a method of modifying the tip portion of the needles and/or channels determined in FIG. 4 based on the comparison with the tip portion determined in FIG. 5A according to some embodiments.

In some embodiments, the step 340 may further include steps to modify the starting position(s) of the needles and/or channels determined in FIG. 4 with the starting position(s) of the needles and/or channels determined in FIG. 5A. FIG. 5B shows an example of a method 550 of modifying the starting position(s) of the needles and/or channels determined in FIG. 4 based on the comparison according to some embodiments. For example, the method 550 may include a step 560 of comparing the starting position(s) of the whole needles and/or channels determined in FIG. 4 with the respective starting position(s) determined in FIG. 5A to determine whether they match. If they match (Yes at step 570), then no further processing is necessary (step 580) and the needle locations determined in FIG. 4 may be outputted in step 340 for further processing by the method 300. If it is determined that the starting position(s) do not match, then the locations determined in FIG. 4 may be further processed based on the difference between the starting positions. For example, if it is determined that the starting position of the whole channel(s) and/or needle(s) determined in FIG. 4 is shorter than the respective starting (tip) position in FIG. 5A (e.g., because there is a position gap between the tip portion of the needle and/or channel determined in FIG. 4 and the tip portion determined in FIG. 5A), the method 550 may further include a step 572 of interpolating (extending) the whole needle (e.g., body portion and the tip portion) determined in FIG. 4 till the starting (tip) position of FIG. 4 matches the starting (tip) position determined in FIG. 5A. This can resolve the missing part of the needle and/or channel due to artifacts in the ultrasound images that may have occurred when the needle and/or channel locations are determined in the method of FIG. 4. If the starting position of a whole needle and/or channel detected in the method of FIG. 4 is determined to be longer (e.g., extend past) the starting (tip) position determined in the method of FIG. 5A, the step 550 may include a step 574 of removing or deleting that part of the needle and/or channel determined in FIG. 4 so that it matches with the respective starting (tip) position determined in FIG. 5A. This can resolve any over-detection due to artifacts in ultrasound images that may have occurred when the needle/channel locations are determined according the method of FIG. 4. The location of the needles and/or channels determined in the steps 572 and/or 574 may be outputted in step 340 for further processing by the method 300.

In step 342, for reconstructing the needles and/or channels of the applicator(s) in the planning images (e.g., CT images), the locations of the needles and/or channels of the applicators may be determined in the planning images (e.g., CT) by reconstruction. In some embodiments, the step may include filtering the intensity using a threshold to detect the needles and/or channels. This threshold may be based on the applicator diameter. In some embodiments, the threshold may be about 950 HU. In some embodiments, other methods may be used.

In some embodiments, the method 300 may include a step 350 of registering the locations of the needles and/or channels of the applicator(s) between the ultrasound images determined in step 340 and the planning images determined in step 342 to determine a transformation field to transform target (e.g. prostate) contour in ultrasound images to planning (e.g. CT) images. In this way, the needles and/or channels can serve as landmark to fuse the US and planning images.

Figure 6:
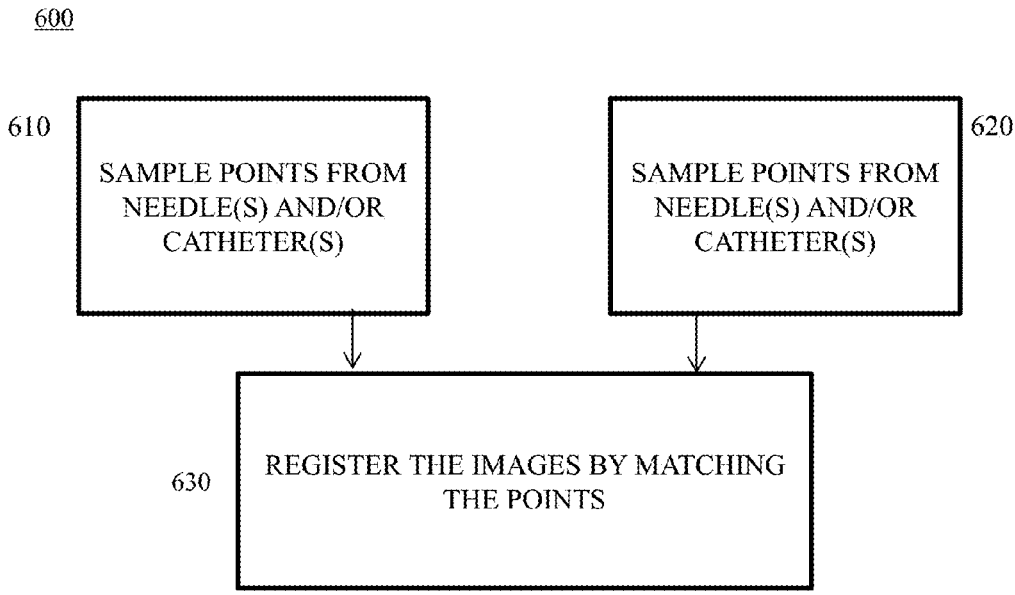
FIG. 6 shows a method of registering the ultrasound image data and planning image data based on the needle and/or channel locations of the applicator(s) according to embodiments.

In some embodiments, the ultrasound images and the planning images may be registered according to the method shown in FIG. 6. FIG. 6 shows a method 600 of registering the US image and the planning images. In other embodiments, other registration methods may be used.

In some embodiments, the method 600 may include a step 610 of sampling points from the needles and/or channels of the applicator(s) determined from the post-operative ultrasound image data and a step 620 of sampling points from the needles and/or channels of the applicator(s) from the planning image data based on the locations of the needles and/or channels determined in steps 340 and 342, respectively. In some embodiments, the points may be sampled using a local distinctiveness measure. In other words, less sample points can be required in areas of small changes (smooth areas), while more sample points can be required in areas of greater changes. Please see, e.g., Alexa M, Behr J, Cohen-Or D, Fleishman S, Levin D, Silva C T. Computing and rendering point set surfaces. Visualization and Computer Graphics, IEEE Transactions on. 2003; 9(1):3-15. doi: 10.1109/tvcg.2003.1175093; and Torsello A, Rodola, x, E., Albarelli A, editors. Sampling Relevant Points for Surface Registration. 3D Imaging, Modeling, Processing, Visualization and Transmission (3DIMPVT), 2011 International Conference on; 2011 16-19 May 2011. Next, the method 600 may include a step 630 of registering the images by matching the points from the ultrasound images and the planning images. In some embodiments, the points may be matched using a fuzzy-to-deterministic method. In some embodiments, the correspondences between the two point sets may be described by fuzzy correspondence matrixes. The similarity between two sets of applicator landmarks in US (e.g., TRUS images) and planning images (e.g., CT images) can be defined by a Euclidean distance between their point sets. A soft assign technique may then be used to optimize the fuzzy correspondence matrixes to minimize the Euclidean distance between their point sets. In some embodiments, other methods may be used.

The method 300 may include a step 360 of integrating the US-based target contours determined in step 330 and the planning images received in step 320 to generate integrated planning images. In some embodiments, the step 360 may include transforming the US-based target contours (e.g., volume determined in step 330) using the transformation field (determined in step 350) from US-planning image registration. In some embodiments, the transformation may be B-Spline spatial transformation. In other embodiments, the transformation may be a different transformation method.

In some embodiments, the method may further include a step 370 of outputting the generated integrated image(s). In some embodiments, the outputting may include displaying, printing, storing, and/or transmitting the generated image(s). In some embodiments, the integrated image(s) may be transmitted to another system, server and/or storage device for the printing, displaying and/or storing the generated images.

In some embodiments, the method may further include transmitting the generated image(s) to another system. In some embodiments, the method may further include transmitting the generated images to a treatment planning system, such as HDR treatment planning system 140.

Figure 7:
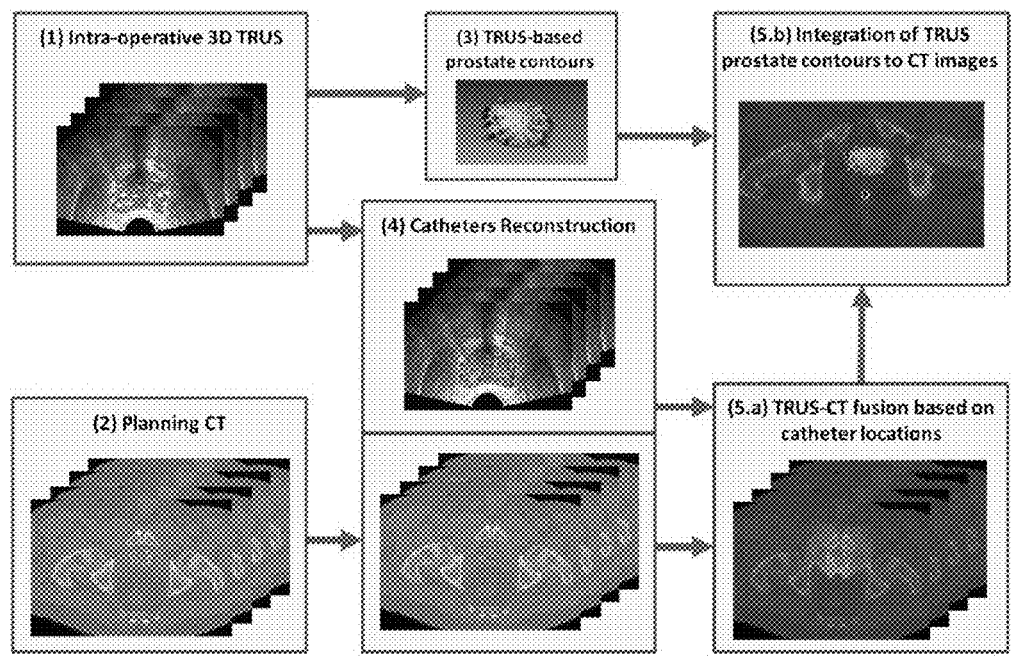
FIG. 7 shows an illustrative method of processing ultrasound image data and planning image data to generate an integrated image according to embodiments.
Figure 8:
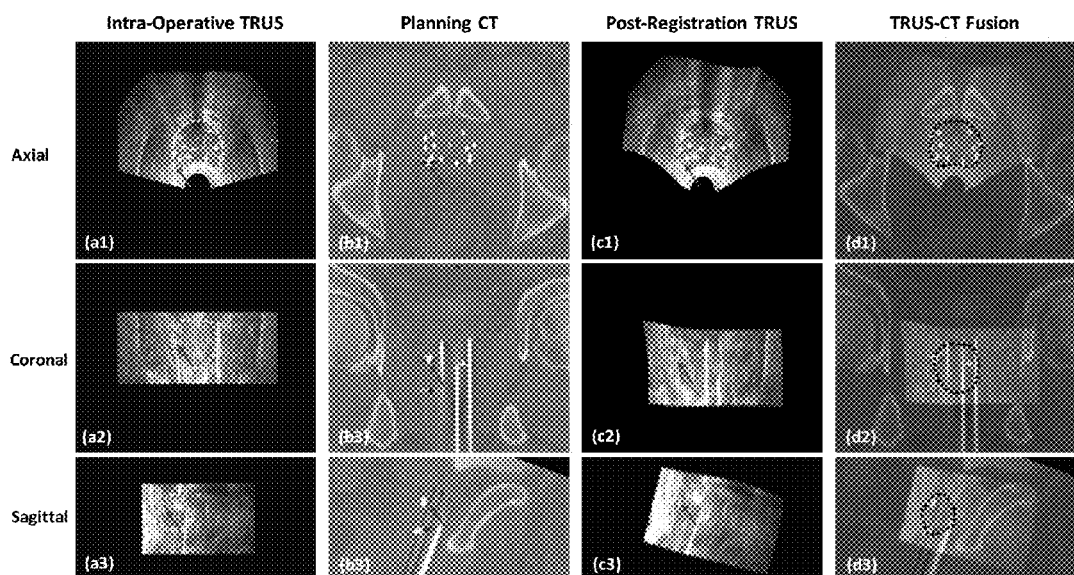
FIG. 8 shows an example of results of integrating TRUS-based prostate volume into planning images (post-operative CT images).

FIG. 7 shows an illustrative overview of the method integrating TRUS-based prostate volume into planning images based on the needle and/or channels of the applicator(s). FIG. 8 shows an example of results of integrating TRUS-based prostate volume into planning images (post-operative CT images). In FIG. 8, a1-a3 are TRUS images in axial, coronal and sagittal directions; b1-b3 are the post-operative CT; c1-c3 are the post-registration TRUS images; and d1-d3 are the TRUS-CT fusion images, where the prostate volume is integrated.

In some embodiments, the steps of the methods may be performed over a wired, wireless, or combination thereof. In some embodiments, the networks may be encrypted. In some embodiments, the wired network may be, but is not limited to, a local area network, such as Ethernet, or wide area network. In some embodiments, the wireless network may be, but is not limited to, any one of a wireless wide area network, a wireless local area network, a Bluetooth network, a radio frequency network, or another similarly functioning wireless network.

While the disclosure has been described in detail with reference to exemplary embodiments, those skilled in the art will appreciate that various modifications and substitutions may be made thereto without departing from the spirit and scope of the disclosure as series forth in the appended claims. For example, elements and/or features of different exemplary embodiments may be combined with each other and/or substituted for each other within the scope of this disclosure and appended claims.

What is claimed is:

1. A computer-implemented method for generating an integrated image based on one or more applicators inserted into a target of a patient, each applicator including at least one channel and/or needle, comprising:

receiving ultrasound image data and planning image data of the target of the patient, the ultrasound image data including (i) a first set of ultrasound image data of the target before insertion of the one or more applicators and (ii) a second set of ultrasound image data of the target after the insertion of the one or more applicators and before application of one or more sources into the one or more applicators, the planning image data including image data of the target after the insertion of the planning image data being acquired from an imaging system different from ultrasound;

processing the ultrasound image data to determine a location of each channel and/or needle, the processing including registering the first set of ultrasound image data and the second set of ultrasound image data;

processing the planning image data to determine a location of each channel and/or needle; and generating an integrated image including the ultrasound image data and the planning image data based on the location of each channel and/or needle;

wherein each channel and/or needle includes a body portion and a tip portion;

wherein the processing the ultrasound image data includes:

determining a location of a body portion and a tip portion of each needle and/or channel based on the first set of ultrasound image and the second set of ultrasound image data;

determining a location of a tip portion of each needle and/or channel based on the second set of ultrasound image data;

comparing the location of the body portion and the tip portion of each needle and/or channel determined based on the first set of ultrasound image and the second set of ultrasound image data and the location of the tip portion of each needle and/or channel determined based on the second set of ultrasound image data; and determining to modify the location of the body portion and the tip portion determined based on the first set of ultrasound image data and the second set of ultrasound image data based on the comparison; and wherein the determining the location of the body portion and the tip portion of each needle and/or channel based on the first set of ultrasound image data and the second set of ultrasound image data includes:

registering the first set of ultrasound image data and the second set of ultrasound image data;

generating an attenuation correction map based on the first set of ultrasound image data;

transforming the attenuation correction map to second set of ultrasound image data to generate a corrected second set of ultrasound image data; and determining the location of each channel and/or needle from the corrected second set of ultrasound image data.

2. The method according to claim 1, further comprising:
processing the first set of ultrasound image data to generate a correction map; and
applying the correction map to the second set of ultrasound image data to determine the location of each channel and/or needle of the one or more applicators.

3. The method according to claim 1, wherein the generating the integrated image includes:
sampling a plurality of points from each channel and/or needle from the second set of ultrasound image data and the planning image data based on the location of each channel and/or needle; and
registering the ultrasound image data and the planning image data based on the plurality of points.

4. The method according to claim 1, wherein the planning image data is acquired by a CT imaging system.

5. The method according to claim 1, wherein the determining the location of the tip portion of each needle and/or channel is based on the corrected second set of ultrasound image data.

6. The method according to claim 1, wherein the target is a prostate of the patient.

7. A non-transitory computer readable storage medium comprising program instruction stored thereon, wherein the program instructions are executable by a computer to cause the computer to generating an integrated image based on one or more applicators inserted into a target of a patient, each applicator including at least one channel and/or needle, by performing steps comprising:
receiving ultrasound image data and planning image data of the target of the patient, the ultrasound image data including (i) a first set of ultrasound image data of the target before insertion of the one or more applicators and (ii) a second set of ultrasound image data of the target after the insertion of the one or more applicators and before application of one or more sources into the one or more applicators, the planning image data including image data of the target after the insertion of the planning image data being acquired from an imaging system different from ultrasound;
processing the ultrasound image data to determine a location of each channel and/or needle, the processing including registering the first set of ultrasound image data and the second set of ultrasound image data;
processing the planning image data to determine a location of each channel and/or needle; and
generating an integrated image including the ultrasound image data and the planning image data based on the location of each channel and/or needle;
wherein each channel and/or needle includes a body portion and a tip portion;
wherein the processing the ultrasound image data includes:
determining a location of a body portion and a tip portion of each needle and/or channel based on the first set of ultrasound image and the second set of ultrasound image data; and
determining a location of a tip portion of each needle and/or channel based on the second set of ultrasound image data;
comparing the location of the body portion and the tip portion of each needle and/or channel determined based on the first set of ultrasound image and the second set of ultrasound image data and the location of the tip portion of each needle and/or channel determined based on the second set of ultrasound image data; and
determining to modify the location of the body portion and the tip portion determined based on the first set of ultrasound image data and the second set of ultrasound image data based on the comparison; and
wherein the determining the location of the body portion and the tip portion of each needle and/or channel based on the first set of ultrasound image data and the second set of ultrasound image data includes:
registering the first set of ultrasound image data and the second set of ultrasound image data;
generating an attenuation correction map based on the first set of ultrasound image data;
transforming the attenuation correction map to second set of ultrasound image data to generate corrected second set of ultrasound image data; and
determining the location of each channel and/or needle from the corrected second set of ultrasound image data.

8. The non-transitory computer readable storage medium according to claim 7, further comprising program instructions that, when executed by the computer, cause the computer to perform steps comprising:
processing the first set of ultrasound image data to generate a correction map; and
applying the correction map to the second set of ultrasound image data to determine the location of each channel and/or needle of the one or more applicators.

9. The non-transitory computer readable storage medium according to claim 7, wherein the generating the integrated image includes:
sampling a plurality of points from each channel and/or needle from the second set of ultrasound image data and the planning image data based on the location of each channel and/or needle; and
registering the ultrasound image data and the planning image data based on the plurality of points.

10. The non-transitory computer readable storage medium according to claim 7, wherein the planning image data is acquired by a CT imaging system.

11. The non-transitory computer readable storage medium according to claim 7, wherein the determining the location of the tip portion of each needle and/or channel is based on the corrected second set of ultrasound image data.

12. The non-transitory computer readable storage medium according to claim 7, wherein the target is the prostate.

13. A system for generating an integrated image based on one or more applicators inserted into a target of a patient, each applicator including at least one channel and/or needle, the system comprising:
at least one processor; and
a memory, wherein the processor is configured to cause:
receiving ultrasound image data and planning image data of the target of the patient, the ultrasound image data including (i) a first set of ultrasound image data of the target before insertion of the one or more applicators and (ii) a second set of ultrasound image data of the target after the insertion of the one or more applicators and before application of one or more sources into the one or more applicators, the planning image data including image data of the target after the insertion of the planning image data being acquired from an imaging system different from ultrasound;

processing the ultrasound image data to determine a location of each channel and/or needle, the processing including registering the first set of ultrasound image data and the second set of ultrasound image data;

processing the planning image data to determine a location of each channel and/or needle; and generating an integrated image including the ultrasound image data and the planning image data based on the location of each channel and/or needle;

wherein each channel and/or needle includes a body portion and a tip portion;

wherein the processing the ultrasound image data includes:
  determining a location of a body portion and a tip portion of each needle and/or channel based on the first set of ultrasound image and the second set of ultrasound image data; and
  determining a location of a tip portion of each needle and/or channel based on the second set of ultrasound image data;
  comparing the location of the body portion and the tip portion of each needle and/or channel determined based on the first set of ultrasound image and the second set of ultrasound image data and the location of the tip portion of each needle and/or channel determined based on the second set of ultrasound image data; and
  determining to modify the location of the body portion and the tip portion determined based on the first set of ultrasound image data and the second set of ultrasound image data based on the comparison; and wherein the determining the location of the body portion and the tip portion of each needle and/or channel based on the first set of ultrasound image data and the second set of ultrasound image data includes:
  registering the first set of ultrasound image data and the second set of ultrasound image data;
  generating an attenuation correction map based on the first set of ultrasound image data;
  transforming the attenuation correction map to second set of ultrasound image data to generate corrected second set of ultrasound image data; and
  determining the location of each channel and/or needle from the corrected second set of ultrasound image data.

14. The system according to claim 13, wherein the processor is further configured to cause:
  processing the first set of ultrasound image data to generate a correction map; and
  applying the correction map to the second set of ultrasound image data to determine the location of each channel and/or needle of the one or more applicators.

15. The system according to claim 13, wherein the generating the integrated image includes:
  sampling a plurality of points from each channel and/or needle from the second set of ultrasound image data and the planning image data based on the location of each channel and/or needle; and
  registering the ultrasound image data and the planning image data based on the plurality of points.

16. The system according to claim 13, wherein the planning image data is acquired by a CT imaging system.

* * * * *